(12) United States Patent
Schallmeiner

(10) Patent No.: US 8,268,554 B2
(45) Date of Patent: Sep. 18, 2012

(54) METHOD FOR ANALYTE DETECTION USING PROXIMITY PROBES

(75) Inventor: Edith Schallmeiner, Nyon (CH)

(73) Assignee: Olink AB, Uppsala (SE)

( * ) Notice: Subject to any disclaimer, the term of this patent is extended or adjusted under 35 U.S.C. 154(b) by 810 days.

(21) Appl. No.: 12/294,031

(22) PCT Filed: Mar. 20, 2007

(86) PCT No.: PCT/GB2007/000984
§ 371 (c)(1),
(2), (4) Date: Jan. 16, 2009

(87) PCT Pub. No.: WO2007/107743
PCT Pub. Date: Sep. 27, 2007

(65) Prior Publication Data
US 2010/0021890 A1    Jan. 28, 2010

(30) Foreign Application Priority Data

Mar. 20, 2006 (GB) .................................. 0605584.2

(51) Int. Cl.
*C12Q 1/68* (2006.01)
(52) U.S. Cl. ......... 435/6.1; 435/7.1; 435/7.92; 436/518; 536/24.33
(58) Field of Classification Search ........................ None
See application file for complete search history.

(56) References Cited

U.S. PATENT DOCUMENTS

| | | |
|---|---|---|
| 4,336,173 A | 6/1982 | Ugelstad |
| 4,683,195 A | 7/1987 | Mullis et al. |
| 4,683,202 A | 7/1987 | Mullis |
| 4,800,159 A | 1/1989 | Mullis et al. |
| 4,883,867 A | 11/1989 | Lee et al. |
| 4,965,188 A | 10/1990 | Mullis et al. |
| 5,223,409 A | 6/1993 | Ladner et al. |
| 5,321,130 A | 6/1994 | Yue et al. |
| 5,410,030 A | 4/1995 | Yue et al. |
| 5,436,134 A | 7/1995 | Haugland et al. |
| 5,438,119 A | 8/1995 | Rutter et al. |
| 5,440,016 A | 8/1995 | Blondelle et al. |
| 5,449,603 A | 9/1995 | Nielson et al. |
| 5,463,564 A | 10/1995 | Agrafiotis et al. |
| 5,512,462 A | 4/1996 | Cheng |
| 5,525,735 A | 6/1996 | Gallop et al. |
| 5,534,407 A | 7/1996 | Tabor et al. |
| 5,541,061 A | 7/1996 | Fodor et al. |
| 5,545,568 A | 8/1996 | Ellman |
| 5,549,974 A | 8/1996 | Holmes |
| 5,565,324 A | 10/1996 | Still et al. |
| 5,571,698 A | 11/1996 | Ladner et al. |
| 5,574,656 A | 11/1996 | Agrafiotis et al. |
| 5,582,977 A | 12/1996 | Yue et al. |
| 5,593,853 A | 1/1997 | Chen et al. |
| 5,639,603 A | 6/1997 | Dower et al. |
| 5,641,862 A | 6/1997 | Rutter et al. |
| 5,658,751 A | 8/1997 | Yue et al. |
| 5,684,711 A | 11/1997 | Agrafiotis et al. |
| 5,688,696 A | 11/1997 | Lebl |
| 5,688,997 A | 11/1997 | Baldwin et al. |
| 5,698,673 A | 12/1997 | Blondelle et al. |
| 5,708,153 A | 1/1998 | Dower et al. |
| 5,721,099 A | 2/1998 | Still et al. |
| 5,731,423 A | 3/1998 | Kakarla et al. |
| 5,733,523 A | 3/1998 | Kujipers et al. |
| 5,734,018 A | 3/1998 | Rutter et al. |
| 5,741,713 A | 4/1998 | Brown et al. |
| 5,851,829 A | 12/1998 | Marasco et al. |
| 5,863,753 A | 1/1999 | Haugland et al. |
| 5,965,371 A | 10/1999 | Marasco et al. |
| 5,989,823 A | 11/1999 | Jayasena et al. |
| 6,117,635 A | 9/2000 | Mazarenko et al. |
| 6,248,526 B1 | 6/2001 | Weimer |
| 6,326,145 B1 | 12/2001 | Whitcombe et al. |
| 6,511,809 B2 | 1/2003 | Baez et al. |
| 6,878,515 B1 | 4/2005 | Landegren |

(Continued)

FOREIGN PATENT DOCUMENTS

EP    1 249 500    10/2002

(Continued)

OTHER PUBLICATIONS

Barnes, Wayne M., PCR amplification of up to 35-kb DNA with high fidelity and high yield from λ bacteriophage templates., Proc. Natl. Acad. Sci. USA, vol. 91, pp. 2216-2220, Mar. 1994.
Christenson, et al., Cardiac troponin I measurement with the ACCESS immunoassay system: analytical and clinical performance characteristics, Clinical Chemistry, Jan. 1998; 44(1), pp. 52-60.
Conrad, et al., In vitro selection of nucleic acid aptamers that bind proteins, Methods in Enzymology, vol. 267, 1996, pp. 336-367.
Famulok, M., Bringing picomolar protein detection into proximity, Nature Biotechnology, vol. 20, May 2002, pp. 448-449.
Fitzgerald K., In vitro display technologies—new tools for drug discovery, Drug Discovery Today, vol. 5, No. 6, Jun. 2000, pp. 253-258.
Fredriksson, et al., Protein detection using proximity-dependent DNA ligation assays, Nature Biotechnology, vol. 20, May 2002, pp. 473-477.

(Continued)

*Primary Examiner* — Gary W Counts
(74) *Attorney, Agent, or Firm* — Knobbe Martens Olson & Bear LLP

(57) ABSTRACT

A method for detecting an analyte in a sample, comprising (a) contacting the sample with at least one set of at least first, second and third proximity probes, which probes each include an analyte-binding domain and a nucleic acid domain and can simultaneously bind to the analyte, the nucleic acid domain of the third proximity probe being a splint which is capable of hybridizing at least to the nucleic acid domains of the first and second proximity probes, wherein when all of the at least three proximity probes bind to the analyte, the nucleic acid domains of the first and second proximity probes are conjugatable by means of an interaction mediated by the hybridized splint of the third proximity probe; (b) conjugating the nucleic acids, of the first and second proximity probes; and (c) detecting the conjugation. Also provided is a kit for use in such a method.

28 Claims, 2 Drawing Sheets

U.S. PATENT DOCUMENTS

| | | | | |
|---|---|---|---|---|
| 7,306,904 | B2 * | 12/2007 | Landegren et al. | 435/6.1 |
| 2002/0051986 | A1 | 5/2002 | Baez et al. | |
| 2005/0026180 | A1 | 2/2005 | Willis et al. | |
| 2008/0050743 | A1 | 2/2008 | Sorge et al. | |
| 2011/0136127 | A1 * | 6/2011 | Fredriksson et al. | 435/6.12 |

FOREIGN PATENT DOCUMENTS

| | | |
|---|---|---|
| EP | 1985714 A1 | 10/2008 |
| WO | WO 97/00446 | 1/1997 |
| WO | WO 98/37186 | 8/1998 |
| WO | WO 98/54312 | 12/1998 |
| WO | WO 99/49079 | 9/1999 |
| WO | WO 01/61037 | 8/2001 |
| WO | WO 01/97616 A1 | 12/2001 |
| WO | WO 03/044231 | 5/2003 |
| WO | WO 2005/128963 | 12/2005 |
| WO | WO 2007/044903 A2 | 4/2007 |
| WO | WO 2009/012220 A2 | 1/2009 |

OTHER PUBLICATIONS

Gullberg, et al., Cytokine detection by antibody-based proximity ligation, Proceedings of the National Academy of Sciences of the United States of America, E-pub Jun. 1, 2004, vol. 101, No. 22.

Gustafsdottir, et al., Proximity ligation assays for sensitive and specific protein analyses, Analytical Biochemistry 345 (2005) 2-9, E-pub Feb. 7, 2005.

Hanes, et al., In vitro selection and evolution of functional proteins by using ribosome display, Proc Natl. Acad. Sci. USA, vol. 94, pp. 4937-4942, May 1997.

Heid, et al., Real time quantitative PCR, Genome Res. 1996 6:986-994.

Holland, et al., Detection of specific polymerase chain reaction producted by utilizing the 5' → 3' exonuclease activity of *Thermus aquaticus* DNA polymerase, Proc. Natl. Acad. Sci. USA, vol. 88, pp. 7276-7280, Aug. 1991.

Huang, et al., Fidelity and Predominant Mutations Produced by Deep Vent Wild-Type and Exonuclease-Deficient DNA Polymerases During In Vitro DNA Amplification, DNA and Cell Biology, vol. 15, No. 7, 1996, pp. 589-594.

Lee, et al., Alletic discrimination by nick-translation PCR with fluorogenic probes, Nucleic Acids Research, 1993, vol. 21, No. 16, pp. 3761-3766.

Lind, et al., Development and evaluation of three real-time immuno-PCR assemlages for quantification of PSA, Journal of Immunological Methods, 304(2005), pp. 107-116.

Lundberg, et al., High-fidelity amplificatiom using a thermostable DNA polymerase isolated from *Pyrococcus furiosus*, Gene, 108 (1991) pp. 1-6.

Nazarenko, et al., A closed tube format for amplification and detection of DNA based on energy transfer, Nucleic Acids Research, 1997, vol. 25, No. 12, pp. 16-21.

Perler, et al., Intervening sequences in an Archaea DNA polymerase gene, Proc. Natl. Acad. Sci. USA, vol. 89, pp. 5577-5581, Jun. 1992.

Roberts, Richard W., Totally in vitro protein selection using mRNA-protein fusions and ribosome Display, Current Opinion in Chemical Biology 1999, 3:268-73.

Schaffitzel, et al., Ribosome display: an in vitro method for selection and evolution of antibodies from libraries, Journal of Immunological Methods 231 (1999) 119-35.

Schallmeiner, Edith, Development and Application of Triple Specific Proximity Ligation Assays (3PLA), Digital Comprehensive Summaries of Uppsala Dissertations from the Faculty of Medicine 252, Uppsala, Sweden, May 15, 2007.

Schallmeiner, et al., Sensitive protein detection via triple-binder proximity ligation assays, Nature Methods, vol. 4, No. 12, Feb. 2007, E-pub Dec. 17, 2006.

Schwarz, et al., Improved yields of long PCR products using gene 32 protein, Nucleic Acids Research, vol. 18, No. 4, pp. 1079, 1990.

Tyagi, et al., Molecular beacons: probes that fluoresce upon hybridization, Nature Biotechnology, vol. 14, Mar. 1996, pp. 303-308.

Venge, et al., New generation cardiac troponin I assay for the access immunoassay system, Clinical Chemistry 47, No. 5, 2001, pp. 959-961.

Whitcombe, et al., Detection of PCR products using self-probling amplicons and fluorescence, Nature Biotechnology, vol. 17, Aug. 1999, pp. 804-807.

Zethelius, et al., Troponin I as a predictor of coronary heart disease and mortality in 70-year-old men: a community-based cohort study, Circulation. Feb. 28, 2006;113(8):pp. 1071-1078 E-pub Feb. 20, 2006.

Belyaev, A, et al Enzyme-linked Immuno-PCR. Poster displayed at American Society for Cell Biology meeting, San Francisco Dec. 13, 2008.

Joerger R.D. et al. 1995 "Analyte detection with DNA-labeled antibodies and polymerase chain reaction" *Clin Chem* 41(9):1371-1377.

Olink Bioscience Sep. 20, 2009 "Duolink User Manual: Fluorescence."

Schweitzer B. et al. 2000 "Immunoassays with rolling circle DNA amplification: a versatile platform for ultrasensitive antigen detection" *Proc Natl Aced Sci U S A.* 97(18):10113-10119.

Soderberg, O. et al. 2006 "Direct observation of individual endogenous protein complexes in situ by proximity ligation" *Nat Methods* 3(12):995-1000.

Soderberg O. et al. 2008 "Characterizing proteins and their interactions in cells and tissues using the in situ proximity ligation assay" *Methods* 45(3):227-232.

\* cited by examiner

SEQUENCE LISTING

<160> NUMBER OF SEQ ID NOS: 7

<210> SEQ ID NO 1
<211> LENGTH: 59
<212> TYPE: DNA
<213> ORGANISM: Artificial

-continued

```
<220> FEATURE:
<223> OTHER INFORMATION: oligonucleotide probe

<400> SEQUENCE: 1
cgcatcgccc ttggactacg actgacgaac cgctttgcct gactgatcgc taaatcgtg      59

<210> SEQ ID NO 2
<211> LENGTH: 61
<212> TYPE: DNA
<213> ORGANISM: Artificial Sequence
<220> FEATURE:
<223> OTHER INFORMATION: oligonucleotide probe

<400> SEQUENCE: 2
tcgtgtctaa agtccgttac cttgattccc ctaaccctct tgaaaaattc ggcatcggtg      60
a                                                                     61

<210> SEQ ID NO 3
<211> LENGTH: 53
<212> TYPE: DNA
<213> ORGANISM: Artificial Sequence
<220> FEATURE:
<223> OTHER INFORMATION: oligonucleotide probe

<400> SEQUENCE: 3
tagctaaggc ttagttagac acgagcatta tggagtgcag gatcacgatt tag             53

<210> SEQ ID NO 4
<211> LENGTH: 19
<212> TYPE: DNA
<213> ORGANISM: Artificial Sequence
<220> FEATURE:
<223> OTHER INFORMATION: oligonucleotide probe

<400> SEQUENCE: 4
catcgccctt ggactacga                                                   19

<210> SEQ ID NO 5
<211> LENGTH: 24
<212> TYPE: DNA
<213> ORGANISM: Artificial Sequence
<220> FEATURE:
<223> OTHER INFORMATION: oligonucleotide

<400> SEQUENCE: 5
gggaatcaag gtaacggact ttag                                             24

<210> SEQ ID NO 6
<211> LENGTH: 19
<212> TYPE: DNA
<213> ORGANISM: Artificial Sequence
<220> FEATURE:
<223> OTHER INFORMATION: oligonucleotide

<400> SEQUENCE: 6
atcctgcact ccataatgc                                                   19

<210> SEQ ID NO 7
<211> LENGTH: 26
<212> TYPE: DNA
<213> ORGANISM: Artificial Sequence
<220> FEATURE:
<223> OTHER INFORMATION: oligonucleotide
```

```
<400> SEQUENCE: 7
tacttagaca cgacacgatt tagttt                                          26
```

METHOD FOR ANALYTE DETECTION USING PROXIMITY PROBES

This application is U.S. National Phase of International Application PCT/GB2007/000984, filed Mar. 20, 2007 designating the U.S., and published in English as WO 2007/107743 on Sep. 27, 2007, which claims priority to Great Britain Patent Application No. 0605584.2, filed Mar. 20, 2006.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is SEQUENCE.txt, the date of creation of the ASCII text file is Sep. 28, 2011, and the size of the ASCII text file is 1.68 KB.

FIELD OF THE INVENTION

The present invention relates to a proximity-probe based detection assay for an analyte in a sample and in particular to an improvement in the splint-based proximity probe interaction mechanism. In such assays proximity probes are used, which bind to the analyte and have nucleic acid domains, or tags, which interact in a proximity-dependent manner upon said analyte binding, generally via ligation, to form a detectable, preferably amplifiable, nucleic acid detection product, or detection tag, by means of which said analyte may be detected. In one format of the method of concern in the present invention the interaction of said domains (tags) requires a splint oligonucleotide to bind to the domains, and mediate their interaction (specifically in the case of ligation, a splint oligonucleotide which hybridises to the domains and acts as a template for the ligation reaction). In the method of the present invention, the proximity probe assay is improved by providing said splint oligonucleotide as the nucleic acid domain of a third proximity probe which may also bind to said analyte, i.e. as a splint which may also bind the analyte (a "binding splint"). Thus, in the present invention the splint for the interaction of said proximity probes (or rather the nucleic acid domains thereof) is provided in "tethered" or "localised" form, by means of being provided coupled to an analyte binder.

DESCRIPTION OF THE RELATED ART

Proximity ligation assays permit the sensitive, rapid and convenient detection or quantification of one or more analytes in a sample by converting the presence of such an analyte into a readily detectable or quantifiable nucleic acid-based signal, and can be performed in homogeneous or heterogeneous formats.

Proximity probes of the art are generally used in pairs, and individually consist of an analyte-binding domain with specificity to the target analyte, and a nucleic acid domain coupled thereto. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites on the analyte, which analyte may consist of a single molecule or a complex of interacting molecules, or may have identical specificities, for example in the event that the target analyte exists as a multimer. When a proximity probe pair come into close proximity with each other, which will primarily occur when both are bound to their respective sites on the same analyte molecule, the nucleic acid domains are able to be joined to form a new nucleic acid sequence by means of a ligation reaction templated by a splint oligonucleotide subsequently added to the reaction, said splint oligonucleotide containing regions of complementarity for the ends of the respective nucleic acid domains of the proximity probe pair. The new nucleic acid sequence thereby generated serves to report the presence or amount of analyte in a sample, and can be qualitatively or quantitatively detected, for example by realtime, quantitative PCR (q-PCR).

WO 97/00446 and U.S. Pat. No. 6,511,809 disclose the heterogeneous use of proximity ligation assays, i.e. the analyte is first immobilised to a solid substrate by means of a specific analyte-binding reagent.

Homogeneous proximity ligation assays (i.e., in solution) are disclosed in WO 01/61037, WO 03/044231, WO 2005/123963, Fredriksson et al (2002) Nat Biotech 20:473-477 and Gullberg et al (2004) Proc Natl Acad Sci USA 101:8420-8424.

Although pairs of proximity probes are generally used, modifications of the proximity probe assay have been described, in e.g. WO 01/61037 and WO 2005/123963, where three proximity probes are used to detect a single analyte molecule, the nucleic acid domain of the third probe possessing two free ends which can be joined (ligated) to the respective free ends of the nucleic acid domains of the first and second probes, such that it becomes sandwiched between them. In this embodiment, two species of splint oligonucleotide are required to template ligation of each of the first and second probes' nucleic acid domains to that of the third.

Proximity ligation assays have proved very useful in the specific and sensitive detection of proteins in a number of different applications, e.g. the detection of weakly expressed or low abundance proteins. However, such assays are not without their problems and room for improvement exists, particularly with respect to the sensitivity of the assay and the detection limit attainable.

The sensitivity of the conventional proximity ligation assays, as described above, is limited by two main factors: (i) the affinity of the analyte-binding domains for the target analyte and (ii) the non-specific background signal arising from the random proximity of non-bound probes, particularly probe pairs. Using probes having binding domains with high affinity for the analyte, sensitivity is limited to the detection of approximately 6000 molecules. In order to achieve a low level of background, very low concentrations of proximity probes must be used. This precludes any attempt to compensate for probes comprising low affinity analyte-binding domains by using higher concentrations of probe. It has therefore been found that this may limit the sensitivity of the assay, and the range over which quantitative results may be obtained.

DETAILED DESCRIPTION OF THE INVENTION

Figure 1:
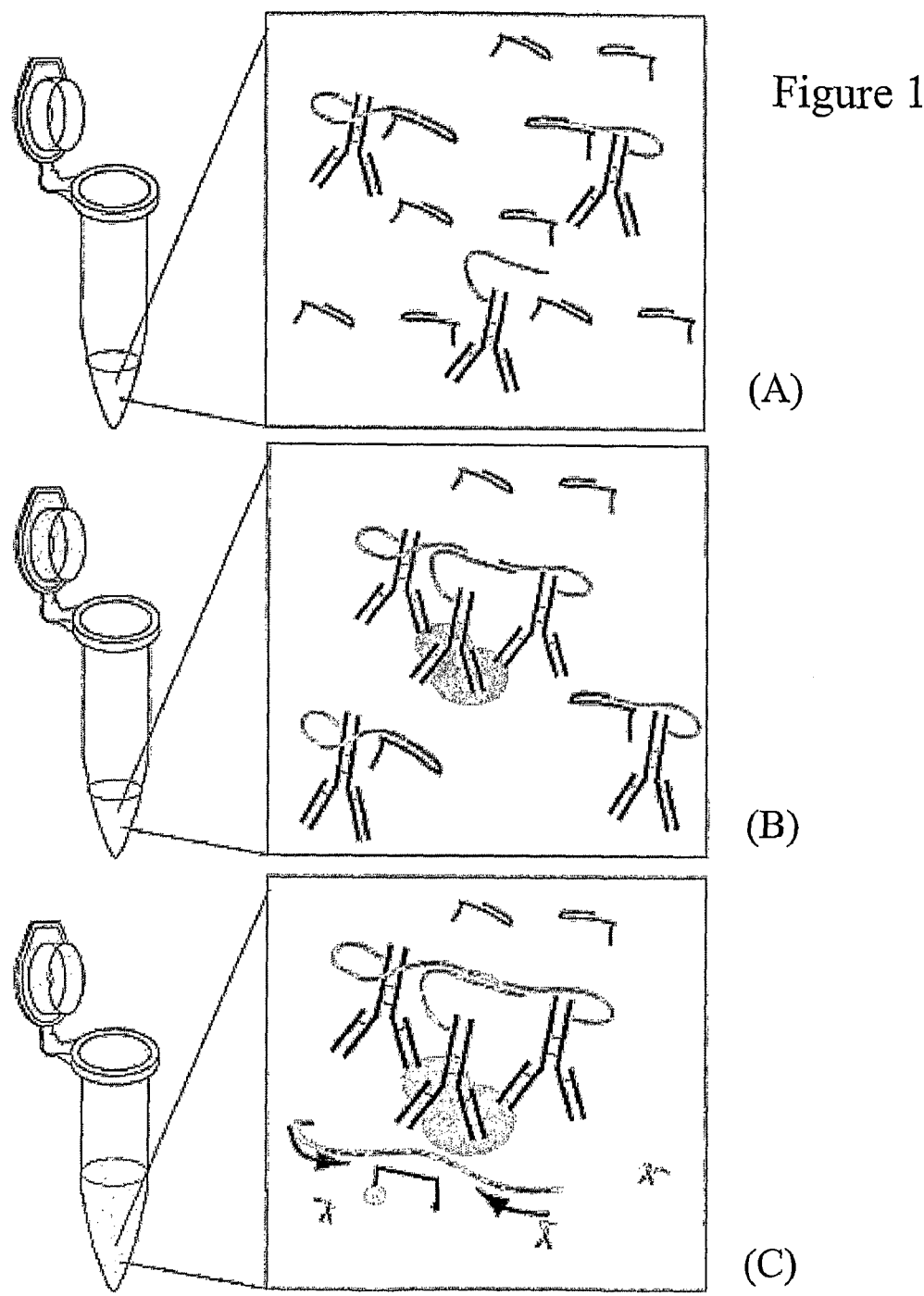
FIG. 1: General scheme for the different steps in the binding splint assay. Blocking of the proximity probes with competition oligonucleotides (A). After the addition of the protein during the incubation time the protein is recognized by the proximity probes and the templating proximity probe outcompetes the blocking oligonucleotides (B) and ligation and detection reaction where the new sequence is formed and detected by q-PCR (C).

In order to overcome the limitations of the proximity ligation assays known in the art, as described above, it has now been found that the use of a third probe, the nucleic acid domain of which contains regions of complementarity for the ends of the nucleic acid domains of the first and second probes and is thereby able to act as a splint to template their ligation, significantly improves the sensitivity and specificity of the assay. By coupling the ligation-templating splint oligonucleotide to a further analyte binding domain, rather than using free splint oligonucleotide, the splint is co-localised within the sample with the first and second probes which it is required to template ligation of, allowing lower concentrations of splint to be used in comparison with assays employing free splint oligonucleotide, with a consequent lowering of non-specific background signal.

The use of such a "binding splint" has further beneficial effects on the performance of the assay. Unlike in the "free splint" assays, the lower background resulting from the use of lower concentrations of splint in the method of the present invention allows for higher concentrations of the first and second probe to be used, further increasing sensitivity and permitting compensation of low affinity probes. Increased specificity arises from the requirement that three binding events must occur, and sensitivity is enhanced over two-probe assays by virtue of the fact that three probes are less likely to come into close proximity by chance (i.e., non-specifically) than are two probes.

Furthermore, since the binding splint (third probe) is added to the reaction at the same time as the first and second probes, the three probes can interact immediately when brought into close proximity through binding to the analyte. This produces an avidity effect by reducing the dissociation rate of, and thereby acting to stabilise, the analyte-probe complex, increasing the conversion rate of analyte- to DNA-signal and thus the sensitivity of the assay. This provides a significant advantage over the free splint assays known in the art, in which the splint is added at the ligation step, subsequent to the binding step, and in which therefore binding and dissociation of individual probes occurs independently.

As shown in more detail in the Examples below, the present invention represents a significant advance over the free splint proximity ligation assays known in the art, with significantly fewer target analytes being detectable. For example, as described in Example 1 below, as few as 60 molecules of vascular endothelial growth factor (VEGF) protein may be detected.

Accordingly, in one aspect the present invention provides a method for detecting an analyte in a sample, comprising:

(a) contacting said sample with at least one set of at least first, second and third proximity probes, which probes each comprise an analyte-binding domain and a nucleic acid domain and can simultaneously bind to the analyte, the nucleic acid domain of said third proximity probe being a splint which is capable of hybridising at least to the nucleic acid domains of said first and second proximity probes, wherein when all of the at least three proximity probes bind to said analyte, the nucleic acid domains of said first and second proximity probes are conjugatable by means of an interaction mediated by said hybridised splint;

(b) conjugating the nucleic acids of said first and second proximity probes; and (c) detecting said conjugation.

The method of the invention depends upon detecting the presence of an analyte in a sample by detecting the interaction between two (or more) proximity probes, when such probes are bound to the analyte. The interaction between the probes (or more specifically, between their respective nucleic acid domains) is thus proximity-dependent; the binding of the detection probes, together, on the analyte brings them into proximity, such that they (or more particularly, their nucleic acid domains) may interact. Accordingly, by detecting the interaction (or conjugation), the analyte may be detected. In the method of the invention, the proximity probes may interact by being conjugated, or joined to one another, and the splint assists in or mediates this interaction (conjugation). The conjugation may be detected by detecting the conjugation product (interaction product).

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g., through generation of a standard curve). Alternatively, relative quantification can be accomplished by comparison of detected levels or amounts between two or more different target analytes to provide a relative quantification of each of the two or more different analytes, i.e., relative to each other.

The "analyte" may be any substance (e.g. molecule) or entity it is desired to detect by the method of the invention. The analyte is the "target" of the assay method of the invention. The analyte may accordingly be any biomolecule or chemical compound it may be desired to detect, for example a peptide or protein, or nucleic acid molecule or a small molecule, including organic and inorganic molecules. The analyte may be a cell or a microorganism, including a virus, or a fragment or product thereof. It will be seen therefore that the analyte can be any substance or entity for which a specific binding partner (e.g., an affinity binding partner) can be developed. All that is required is that the analyte is capable of simultaneously binding three binding partners (more particularly, the analyte-binding domains of at least three proximity probes). Proximity probe-based assays, such as that of the present invention, have found particular utility in the detection of proteins or polypeptides. Analytes of particular interest may thus include proteinaceous molecules such as peptides, polypeptides, proteins or prions or any molecule which includes a protein or polypeptide component, etc., or fragments thereof. The analyte may be a single molecule or a complex that contains two or more molecular subunits, which may or may not be be covalently bound to one another, and which may be the same or different. Thus in addition to cells or microrganisms, such a complex analyte may also be a protein complex. Such a complex may thus be a homo- or hetero-multimer. Aggregates of molecules e.g. proteins may also be target analytes, for example aggregates of the same protein or different proteins. The analyte may also be a complex between proteins or peptides and nucleic acid molecules such as DNA or RNA. Of particular interest may be the interactions between proteins and nucleic acids, e.g. regulatory factors, such as transcription factors, and DNA or RNA.

All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc), tissues, biopsies, cell cultures, cell suspensions, conditioned media or other samples of cell culture constituents, etc. The sample may be pre-treated in any convenient or desired way to prepare for use in the method of the invention, for example by cell lysis or purification, isolation of the analyte, etc.

The proximity probes for use in the method of the invention comprise an analyte-binding domain and a nucleic acid domain, and are in effect detection probes which bind to the analyte (via the analyte-binding domain), the binding of which may be detected (to detect the analyte) by means of detecting the interaction which occurs between the nucleic acid domains thereof upon such binding. Accordingly the probes may be viewed as nucleic acid-tagged affinity ligands or binding partners for the analyte, the analyte-binding domain being the affinity binding partner, and the nucleic acid domain the nucleic acid tag. The nucleic acid domain is coupled to the analyte-binding domain and this "coupling" or connection may be by any means known in the art, and which may be desired or convenient and may be direct or indirect e.g. via a linking group. For example, the domains may be associated with one another by covalent linkage (e.g. chemical cross-linking) or by non-covalent association e.g., via streptavidin-biotin based coupling (biotin being provided on one domain and streptavidin on the other).

The analyte binding domain may be any binding partner for the target analyte, and it may be a direct or indirect binding partner therefor. Thus it may bind to the target analyte directly, or indirectly via an intermediary molecule or binding partner which binds to the target analyte, the analyte binding domain binding to said intermediary molecule (binding partner). Particularly, the analyte-binding domain or the intermediary binding partner is a specific binding partner for the analyte. A binding partner is any molecule or entity capable of binding to its target, e.g. target analyte, and a specific binding partner is one which is capable of binding specifically to its target (e.g. the target analyte), namely that the binding partner binds to the target (e.g. analyte) with greater affinity and/or specificity than to other components in the sample. Thus binding to the target analyte may be distinguished from non-target analytes; the specific binding partner either does not bind to non-target analytes or does so negligibly or non-detectably or any such non-specific binding, if it occurs, may be distinguished. The binding between the target analyte and its binding partner is typically non-covalent.

The analyte binding domain may be selected to have a high binding affinity for a target analyte. By high binding affinity is meant a binding affinity of at least about $10^{-4}$ M, usually at least about $10^{-6}$ M or higher, e.g., $10^{-9}$ M or higher. The analyte binding domain may be any of a variety of different types of molecules, so long as it exhibits the requisite binding affinity for the target protein when present as part of the proximity probe. In other embodiments, the analyte binding domain may be a ligand that has medium or even low affinity for its target analyte, e.g., less than about $10^{-4}$ M.

The analyte binding domain may be a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand ranging in size from about 10,000 daltons or greater in molecular weight.

The small molecule may be any molecule, as well as a binding portion or fragment thereof, that is capable of binding with the requisite affinity to the target analyte. Generally, the small molecule is a small organic molecule that is capable of binding to the target analyte of interest. The small molecule will include one or more functional groups necessary for structural interaction with the target analyte, e.g. groups necessary for hydrophobic, hydrophilic, electrostatic or even covalent interactions. Where the target analyte is a protein, the small molecule ligand will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, preferably at least two of the functional chemical groups. The small molecule may also comprise a region that may be modified and/or participate in covalent linkage to the nucleic acid domain of the proximity probe, without substantially adversely affecting the small molecule's ability to bind to its target analyte.

Small molecule affinity ligands often comprise cyclical carbon or heterocyclic structures and/or aromatic or polyaromatic structures substituted with one or more of the above functional groups. Also of interest as small molecules are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc, to produce structural analogs.

As such, the small molecule may be obtained from a library of naturally occurring or synthetic molecules, including a library of compounds produced through combinatorial means, i.e. a compound diversity combinatorial library. When obtained from such libraries, the small molecule employed will have demonstrated some desirable affinity for the protein target in a convenient binding affinity assay. Combinatorial libraries, as well as methods for their production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

The analyte binding domain may also be a large molecule. Of particular interest as large molecule analyte binding domains are antibodies, as well as binding fragments and derivatives or mimetics thereof. Where antibodies are the analyte binding domain, they may be derived from polyclonal compositions, such that a heterogeneous population of antibodies differing by specificity are each "tagged" with the same tag nucleic acid (nucleic acid domain) or monoclonal compositions, in which a homogeneous population of identical antibodies that have the same specificity for the target analyte are each tagged with the same tag nucleic acid. As such, the analyte binding domain may be either a monoclonal or polyclonal antibody. In yet other embodiments, the affinity ligand is an antibody binding fragment or derivative or mimetic thereof, where these fragments, derivatives and mimetics have the requisite binding affinity for the target analyte. For example, antibody fragments, such as Fv, F(ab)$_2$ and Fab may be prepared by cleavage of the intact protein, e.g. by protease or chemical cleavage. Also of interest are recombinantly or synthetically produced antibody fragments or derivatives, such as single chain antibodies or scFvs, or other antibody derivatives such as chimeric antibodies or CDR-grafted antibodies, where such recombinantly or synthetically produced antibody fragments retain the binding characteristics of the above antibodies. Such antibody fragments or derivatives generally include at least the VH and VL domains of the subject antibodies, so as to retain the binding characteristics of the subject antibodies. Such antibody fragments, derivatives or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments, derivatives and mimetics thereof may be obtained from commercial sources and/or prepared using any convenient technology, where methods of producing polyclonal antibodies, monoclonal antibodies, fragments, derivatives and mimetics thereof, including recombinant derivatives thereof, are known to those of the skill in the art.

Also suitable for use as binding domains are polynucleic acid aptamers. Polynucleic acid aptamers may be RNA oligonucleotides which may act to selectively bind proteins, much in the same manner as a receptor or antibody (Conrad et al., Methods Enzymol. (1996), 267(Combinatorial Chemistry), 336-367). In certain embodiments where the analyte binding domain is a nucleic acid, e.g., an aptamer, the target analyte is not a nucleic acid.

Importantly, the analyte binding domain will be one that includes a moiety that can be covalently attached to the nucleic acid domain without substantially abolishing the binding affinity of the analyte binding domain to its target analyte.

In addition to antibody-based peptide/polypeptide or protein-based binding domains, the analyte binding domain may also be a lectin, a soluble cell-surface receptor or derivative thereof, an affibody or any combinatorially derived protein or peptide from phage display or ribosome display or any type of combinatorial peptide or protein library. Combinations of any analyte-binding domain may be used.

The binding sites on the analyte for the respective analyte-binding domains of the proximity probes in a set may be the same or different. Thus, for example in the case of a homomeric protein complex or aggregate comprising two or more identical subunits or protein constituents, the analyte-binding domains of two or more probes may be the same. Where the analyte is a single molecule or comprises different sub-units or constituents (e.g. a heteromeric complex or an aggregate of different proteins), the analyte binding domains will be different.

Since the length of the nucleic acid domain of the proximity probes can be constructed to span varying molecular distances, binding sites on the analyte for the analyte binding domain need not be on the same molecule. They may be on separate, but closely positioned, molecules. For example, the multiple binding domains of an organism, such as a bacteria or cell, or a virus, can be targeted by the methods of the present invention.

As noted above, the analyte-binding domain may bind to the analyte directly or indirectly. In the case of indirect binding, the target analyte may first be bound by a specific binding partner (or affinity ligand), and the analyte-binding domain of the proximity probe may bind to the specific binding partner. This enables the design of proximity probes as universal reagents. For example the analyte-specific binding partner may be an antibody, and a universal proximity probe set may be used to detect different analytes by binding to the Fc regions of the various different analyte-specific antibodies.

The nucleic acid domains of the first and second proximity probes may be regarded as the nucleic acid "tags" which interact to form a detectable product, which may be detected to report the detection of the analyte. The nucleic acid domains may thus be regarded as reactive nucleic acid functionalities which interact to provide the signal by means of which the analyte is detected (more particularly to form a signal-giving product). Put another way, the nucleic acid domains may be regarded as "detection tags", which interact to form a "detectable" tag or product. When two or more analytes are present in the same sample they may be detected simultaneously using two or more sets of proximity probes, each set of proximity probes being designed to form on interaction a unique nucleic acid sequence "detectable tag". These unique "detectable tags" may be detected and quantified (optionally after amplification) separately using methods well known in the literature including liquid chromatography, electrophoresis, mass spectrometry, DNA array technology and multi-colour real-time PCR.

In the method of the present invention, the nucleic acid domains of the first and second proximity probes may be conjugated together. As explained further below, this conjugation may be direct, i.e. the respective nucleic acid domains may be directly joined to one another, or it may be indirect, i.e. the respective nucleic acid domains may be joined indirectly e.g. by joining each to one of the two ends of a further intermediary nucleic acid molecule (e.g. oligonucleotide). This "conjugation" or "interaction" is mediated by the splint, which is provided as the nucleic acid domain of the third proximity probe, as explained further below. The conjugation results in the formation of a new nucleic acid molecule or sequence, which may be detected.

As mentioned above, and discussed further below, the nucleic acid domain of the third proximity probe is a splint which hybridises to the nucleic acid domains of the first and second proximity probes, enabling their conjugation (or interaction).

The nucleic acid domains may be a single stranded nucleic acid molecule (e.g. an oligonucleotide), a partially double stranded and partially single stranded molecule, or a double stranded molecule that includes of a region that is double stranded and a region where the two nucleic acid strands are not complementary and therefore single stranded. As such, in certain embodiments, the nucleic acid domain is made up of a single stranded nucleic acid. In other embodiments, the nucleic acid domain may be made up of two partially complementary nucleic acid strands, where the two strands include a hybridized region and non-hybridized region.

The nucleic acid domains are generally of a length sufficient to allow splint-mediated interaction with the nucleic acid domain of another proximity probe when bound to a target analyte. Nucleic acid domains are usually in the range of between about 8 up to about 1000 nucleotides in length, where in certain embodiments they may range from about 8 to about 500 nucleotides in length including from about 8 to about 250 nucleotides in length, e.g., from about 8 to about 160 nucleotides in length, such as from about 12 to about 150 nucleotides in length, from about 14 to about 130 nucleotides in length, from about 16 to about 110 nucleotides in length, from about 8 to about 90 nucleotides in length, from about 12 to about 80 nucleotides in length, from about 14 to about 75 nucleotides in length, from about 16 to about 70 nucleotides in length, from about 16 to about 60 nucleotides in length, and so on. In certain representative embodiments, the nucleic acid domain may range in length from about 10 to about 80 nucleotides in length, from about 12 to about 75 nucleotides in length, from about 14 to about 70 nucleotides in length, from about 34 to about 60 nucleotides in length, and any length between the stated ranges. In some embodiments, the nucleic acid domains are usually not more than about 28, 29, 30, 31, 32, 33, 34, 35, 36, 37, 38, 39, 40, 41, 42, 44, 46, 50, 55, 60, 65, or 70 nucleotides in length.

The nucleic acid domain may be made up of ribonucleotides and/or deoxyribonucleotides as well as synthetic nucleotide residues that are capable of participating in Watson-Crick type or analogous base pair interactions. Thus, the nucleic acid domain may be DNA or RNA or any modification thereof e.g. PNA or other derivatives containing non-nucleotide backbones.

The sequence of the nucleic acid domain of the first and second proximity probes (i.e. the "detection" nucleic acid domains) may be chosen or selected with respect to the splint, provided on the third proximity probe. Thus, the sequence is not critical as long as the first and second domains may hybridise to the third domain (splint). However, the sequences should be chosen to avoid the occurrence of hybridization events other than between the nucleic acid domains of the first and second proximity probes with that of the third proximity probe. Once the sequence is selected or identified, the nucleic acid domains may be synthesized using any convenient method.

The two components of the proximity probe are joined together either directly through a bond or indirectly through a linking group. Where linking groups are employed, such groups may be chosen to provide for covalent attachment of the nucleic acid and analyte-binding domains through the linking group, as well as maintain the desired binding affinity of the analyte-binding domain for its target analyte. Linking groups of interest may vary widely depending on the analyte-binding domain. The linking group, when present, is in many embodiments biologically inert. A variety of linking groups are known to those of skill in the art and find use in the subject proximity probes. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the nucleic acid or analyte binding moieties. Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject proximity probes include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl[4-azidophenyl]-1,3'-dithiopropionate, N-succinimidyl[4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The proximity probes employed in the subject methods may be prepared using any convenient method. In representative embodiments, nucleic acid domains may be conjugated to the analyte-binding domain, either directly or through a linking group. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the proximity probe include: hydroxy, sulfhydryl, amino, and the like. The particular portion of the different components that are modified to provide for covalent linkage may be chosen so as not to substantially adversely interfere with that component's desired binding affinity for the target analyte. Where necessary and/or desired, certain moieties on the components may be protected using blocking groups, as is known in the art, see e.g. Green & Wuts, Protective Groups in Organic Synthesis (John Wiley & Sons) (1991). Methods for producing nucleic acid/antibody conjugates are well known to those of skill in the art. See e.g. U.S. Pat. No. 5,733,523, the disclosure of which is herein incorporated by reference.

In other embodiments, proximity probes may be produced using in vitro protocols that yield nucleic acid-protein conjugates, i.e. molecules having nucleic acids, e.g. coding sequences, covalently bonded to a protein, i.e. where the analyte-binding domain is produced in vitro from vectors which encode the proximity probe. Examples of such in vitro protocols of interest include: RepA based protocols (see e.g., Fitzgerald, Drug Discov. Today (2000) 5:253-258 and WO 98/37186), ribosome display based protocols (see e.g., Hanes et al., Proc. Natl Acad. Sci. USA (1997) 94:4937-42; Roberts, Curr Opin Chem Biol June 1999; 3: 268-73; Schaffitzel et al., J Immunol Methods Dec. 10, 1999; 231: 119-35; and WO 98/54312), etc.

The nucleic acid domain of the third proximity probe is a splint oligonucleotide which functions to mediate the interaction between the nucleic acid domains of the first and second proximity probes (i.e. the "detection" domains). As noted above, the use of a splint in proximity ligation assays is known in the art. The splint may accordingly be viewed a "connector" oligonucleotide which acts to connect or "hold together" the detection domains of the first and second proximity probes, such they may interact, or may be conjugated together.

In particular the splint hybridises with the nucleic acid domains of the first and second proximity probes. More particularly, the splint hybridises (anneals) simultaneously with the nucleic acid domains of at least the first and second proximity probes. This hybridisation of the nucleic acid domains of all of the set of proximity probes to each other increases the avidity of the probe-target complex upon binding to the target analyte. This avidity effect contributes to the sensitivity of the assay by supporting the formation of signal-giving proximity probe-target analyte complexes.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule. The nucleic acid domains of the first and second proximity probes thus contain a region of complementarity for the nucleic acid domain of the third proximity probe, and conversely the nucleic acid domain of the third proximity probe contains regions of complementarity for each of the nucleic acid domains of the first and second proximity probes.

The regions of complementarity (i.e. hybridisation regions) may have a length in the range of 4-30 bp e.g. 6-20, 6-18, 7-15 or 8-12 bp.

The splint nucleic acid domain is generally of a length sufficient to provide for the above described simultaneous binding of nucleic acid domains of the first and second probes. In representative embodiments, the splint oligonucleotides range in length from about 6 to about 500 nucleotides, including from about 20 to about 40 nucleotides, e.g. from about 25 to about 30 nucleotides.

As noted above, the interaction or conjugation between the nucleic acid domains of the first and second proximity probes is a joining of the respective domains. This joining may preferably be a ligation, particularly a template-directed ligation. In such a case, it will clearly be understood that the ligation template will be provided by the splint. Such a ligation may be carried out using a ligase enzyme.

Thus, in a preferred embodiment of the method of the invention, the nucleic acid domains of the first and second probes are ligatable by means of a reaction templated by the hybridised splint, said nucleic acid domains are ligated and the ligation product is detected. In such an embodiment, the splint may therefore be viewed as a "splint template" or "ligation template" or "template oligonucleotide".

For the interaction, or more particularly ligation, to take place, one of the nucleic acid domains of the first and second proximity probes will typically be coupled to the analyte-binding domain by its 5' end (leaving a free 3' hydroxyl end), while the other domain will be coupled via its 3' end (leaving a free 5' phosphate end). One of the first and second proximity probes will thus be a 5' probe having a free 3' hydroxyl group capable of interacting with the 5' phosphate of the other 3' probe.

To be ligatable, the respective first and second nucleic acid domains hybridise to the splint with the 3' end of one lined up to the 5' phosphate of the other. However, as mentioned above and described in more detail below, the ligation of the respective domains need not be direct and they may be ligated together by means of an intermediary oligonucleotide, or whichever of the first or second proximity probe carries a free 3' nucleic acid domain end may be extended using a polymerase to fill the gap until the first and second nucleic acid domains can be joined by a ligation reaction. Thus, the respective 3' and 5' ends need not be hybridised immediately adjacent to one another on the splint (template) but may hybridise to the splint leaving a space (or a stretch of nucleotides) between them.

The hybridisation of the splint simultaneously to both nucleic acid domains of the first and second proximity produces a stable duplexed structure that contains all three nucleic acid domains. Such a duplexed structure brings together the 3' hydroxyl free end of the nucleic acid domain of the first proximity probe and the 5' phosphoryl free end of the nucleic acid domain of the second proximity probe (although as mentioned above, these need not be immediately adjacently juxtaposed).

Thus, the splint may include a first 3' region of complementarity for the nucleic acid domain of the 5' free proximity probe and a second 5' region of complementarity for the nucleic acid domain of the 3' free proximity probe. The first and second regions of the splint may be 3 to 20, 6 to 17, 6 to 15 or 6 to 12 or 8 to 12 nucleotides in length, e.g. about 13 to 17, 12 to 16, 11 to 15, or 12 to 14 nucleotides in length or about 6 to 12, 7 to 11 or 8 to 10 nucleotides in length.

As will be described in more detail below, amplification of the conjugation product may be used as part of the detection process. Accordingly, it may in some embodiments be desirable to design the splint so as to minimise any false amplification which may take place in such a step, for example any possibility of the splint acting as a template for the polymerase used in the amplification. Thus for example the splint may be provided as an RNA oligonucleotide or a DNA/RNA hybrid; Taq polymerase typically used in amplification reactions cannot use an RNA template. Alternatively, a similar effect may be achieved using a DNA splint with two short hybridisation regions; since the hybridisation is weak, such a splint will not template DNA polymerisation at the high temperatures used in PCR.

As mentioned above, in one embodiment, the nucleic acid domains of the first and second probes may hybridise to the splint not immediately adjacent to each other, but to leave a gap between them. To enable their conjugation (e.g. ligation) a further oligonucleotide, referred to herein as a "cassette oligonucleotide", may hybridise to the splint in this gap, more particularly to span this gap. Such a cassette oligonucleotide may be hybridised with each of its ends directly adjacent to the end of each of the respective domains, such that each such domain end may be conjugated to the cassette oligonucleotide to form a single new nucleic acid product. This requires two conjugation events, both of which are templated by the splint. Both the 5' and the 3' end of the cassette oligonucleotide are joined (e.g. ligated) to the free end of the nucleic acid domain of the first and second probe, as appropriate. The first and second domains are thus connected, or joined, via the cassette oligonucleotide. Such an arrangement may add flexibility to the nucleic acid domains of the probes. The length of the cassette oligonucleotide (and hence the gap between the ends of the first and second domains when hybridised to the splint) may vary, for example between 4 to 50, eg. 6-30, 6-25, 6-22, 8-22, 10-22, 6-20, 8-20, 10-20 nucleotides.

The cassette oligonucleotide, which functions as an intermediary oligonucleotide in the conjugation of the first and second nucleic acid domains, may be added after the probes have been contacted with the sample. Alternatively, it may be added at the same time or it could be pre-hybridized to the third proximity probe.

The gap may also be filled by extending the nucleic acid domain of whichever of the first or second proximity probe carries a free 3' end, using a polymerase. Once the gap has been filled, the ends are joined by a ligation step.

To carry out the method of the invention, the sample is first contacted with at least one set of probes.

In certain embodiments a sample may be assayed for two or more different target analytes. In such embodiments, the sample is contacted with a set of proximity probes for each target analyte, such that the number of sets contacted with the sample may be two or more, e.g., three or more, four or more etc. Such methods find particular use in multiplex and high-throughput applications.

The amount of proximity probes that is added to a sample may be selected to provide a sufficiently low concentration of proximity probe in the reaction mixture to ensure that the proximity probes will not randomly come into close proximity with one another in the absence of binding to a target analyte, at least not to any great or substantial degree. As such, it is intended that only when the proximity probes bind the analyte through the binding interaction between the analyte-binding domains of the proximity probes and the binding sites of the analyte, do the proximity probes come into close proximity to one another. In representative embodiments, the concentration of the proximity probes in the reaction mixture following combination with the sample ranges from about 1 fM to 1 µM, such as from about 1 pM to about 1 nM, including from about 1 pM to about 100 nM.

Following combination of the sample and set(s) of proximity probes, the reaction mixture may be incubated for a period of time sufficient for the proximity probes to bind target analyte, if present, in the sample. In representative embodiments, the product mixture may be incubated for a period of time ranging from about 5 minutes to about 48 hours, including from about 30 minutes to about 12 hours, at a temperature ranging from about 4 to about 50° C., including from about 20 to about 37° C. Conditions under which the reaction mixture is maintained should be optimized to promote specific binding of the proximity probe to the analyte, while suppressing unspecific interaction. Conditions should also allow for efficient and specific hybridization between the nucleic acid domains as described above.

In certain embodiments, the effective volume of the incubation mixture is reduced, at least during the portion of the incubation step in which the proximity probes are binding to target analyte, if present in the sample. In these embodiments, the effective volume of the incubation mixture may be reduced for a number of different reasons. In certain embodiments, the effective volume of the incubation mixture is reduced in order to allow for the use of medium and low affinity analyte-binding domains and/or increase the sensitivity of the assay. For example, in certain embodiments where the effective volume of the incubation mixture is reduced, the analyte-binding domains may be medium or low affinity binders, by which is meant that the analyte-binding domains may have a binding affinity for their target analyte that is less than about $10^{-4}$ M, such as about 1 nM Kd. In certain embodiments, the sensitivity of the assay may be increased such that the assay can detect as few as about 100 or fewer target analytes in a 1 µl sample, including as few as about 75 or fewer target analytes in a 1 µl sample, including as few as about 50 or fewer target analytes in a 1 µl sample.

In certain embodiments, a "crowding agent" or "volume excluder" is included in the mixture during the incubation step reviewed above, e.g., to reduce the effective volume of the incubation mixture during binding of the proximity probes to their target analyte. Typically, the "crowding agent" is a water soluble macromolecular material. Suitable macromolecular materials broadly comprise biocompatible natural or synthetic polymers having an average molecular weight of from about 1500 to several million, which do not specifically interact with the other reagents in the mixture, or the product. Such polymers are known in the art as "volume-excluders", as their primary function is to occupy volume in the in vitro reaction medium and provide a highly concentrated environment for biochemical reactions, e.g., approximating in vivo conditions. The volume-excluding polymers must of course be sufficiently soluble to provide the required concentration. Suitable exemplary polymers include, but are not limited to: commercially available polyethylene glycol (PEG) polymers, e.g., having an average molecular weight greater than about 2000, FICOLL polymers such as those having an average molecular weight of about 70,000, bovine plasma albumin, glycogen, polyvinylpyrrolidone, dextran, etc. PEG polymers of higher molecular weights, especially, PEG 1450, PEG 3350, PEG 6000 (also sold as PEG 8000), and PEG 20,000, having average molecular weights of about 1450, 3000-3700, 6000-7500, and 15,000-20,000, respectively, are employed in representative embodiments. PEG 6000 and PEG 8000 are employed in representative embodiments. The concentration of the volume-excluding polymers in the incubation reaction in representative embodiments falls within a range of about 5% w/v to about 45% w/v, depending upon the type of polymer and its molecular weight. In general, it is expected that a given type of polymer of higher molecular weight need be present in lower concentration than the same type of polymer of lower molecular weight to achieve the same effect on enzyme activity.

In those embodiments where a volume excluder is employed, prior to the next step of the method, the incubation mixture may be diluted to account for the presence of the volume excluder, e.g., by at least about 2-fold or more, such as at least about 5-fold or more, including at least about 10-fold or more, depending on the amount of volume excluder that is present, the nature of the dilution fluid, etc., where in representative embodiments the dilution fluid is water or some other suitable aqueous fluid of water and one or more solutes, e.g., salts, buffering agents, etc.

Instead of, or in addition to, the use of a volume excluder, the incubation mixture may be reduced in volume during incubation by removing a portion of the water from the incubation mixture, e.g., via evaporation. In these embodiments, the volume of the fluid may be reduced by at least about 2-fold or more, such as at least about 5-fold or more, including at least about 10-fold or more, as desired. Importantly, not all of the water is removed from the incubation mixture in these embodiments. Any convenient protocol may be employed for reducing the volume of the incubation mixture by removing a select portion of the water therefrom. An instrument for controlling evaporation rate by monitoring and adjusting humidity and temperature may be employed, where in certain embodiments the volume of the incubation mixture is monitored, e.g., by continuously measuring the volume of the incubation mixture, where when appropriately evaporated, the ligation and PCR-mixes may be added, as described above. As desired, a heating block could be used to enhance the evaporation. Alternatively, the volume of the incubation mixture may be reduced by filtrating out water. In representative embodiments, a size exclusion filter is used to selectively contain molecules of sizes larger than a cut off limit while smaller molecules and water is removed by passage through the filter. The force placed on the solution to move it through the filter may be by either centrifugation or vacuum suction.

Upon binding of the binding domains of the proximity probes to the analyte, the nucleic acid domains of the proximity probes come into close proximity to one another. As a result, the nucleic acid domain (splint) of the third probe is able to bind (hybridise) to the nucleic acid domain of the first and second probes.

Following the combination of the sample with the proximity probes, the cassette oligonucleotide may be added, if used, and allowed to hybridise. The nucleic acid domains of the first and second probes (hybridised to the splint) are then allowed to conjugate, or interact. The reaction mixture is then assayed for the presence of any splint-mediated interaction. Thus, conjugation of the first and second nucleic acid domains is detected, generally by detecting the conjugation product thereof.

In general, any convenient protocol that is capable of detecting the presence of proximity dependent interactions may be employed. The detection protocol may or may not require a separation step.

In one representative embodiment, the splint mediated interaction of the first and second proximity probes (i.e. conjugation) is achieved by nucleic acid ligation of the free 3' hydroxyl and 5' phosphate ends of the nucleic acid domains of the first and second proximity probes, and this interaction is detected by subsequent detection of the ligated product. In these representative embodiments, ligation of the splint stabilised nucleic acid domains of the first and second proximity probes is achieved by contacting the reaction mixture with a nucleic acid ligating activity, e.g. provided by a suitable nucleic acid ligase, and maintaining the mixture under conditions sufficient for ligation of the nucleic acid domains to occur.

As is known in the art, ligases catalyze the formation of a phosphodiester bond between juxtaposed 3'-hydroxyl and 5'-phosphate termini of two immediately adjacent nucleic acids when they are annealed or hybridized to a third nucleic acid sequence to which they are complementary (i.e. a template). Any convenient ligase may be employed, where representative ligases of interest include, but are not limited to: Temperature sensitive and thermostable ligases. Temperature sensitive ligases include, but are not limited to, bacteriophage T4 DNA ligase, bacteriophage T7 ligase, and $E.\ coli$ ligase. Thermostable ligases include, but are not limited to, Taq ligase, Tth ligase, and Pfu ligase. Thermostable ligase may be obtained from thermophilic or hyperthermophilic organisms, including but not limited to, prokaryotic, eukaryotic, or archael organisms. Certain RNA ligases may also be employed in the methods of the invention.

In this ligation step, a suitable ligase and any reagents that are necessary and/or desirable are combined with the reaction mixture and maintained under conditions sufficient for ligation of the hybridized ligation oligonucleotides to occur. Ligation reaction conditions are well known to those of skill in the art. During ligation, the reaction mixture in certain embodiments may be maintained at a temperature ranging from about 4° C. to about 50° C., such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM $MgCl_2$, 10 mM DTT, 1 mM ATP, 25 mg/ml BSA, 0.25 units/ml RNase inhibitor, and T4 DNA ligase at 0.125 units/ml. In yet another representative embodiment, 2.125 mM magnesium ion, 0.2 units/ml RNase inhibitor; and 0.125 units/ml DNA ligase are employed.

Following ligation, the ligation products (ligated nucleic acid domains of the first and second probes) are detected as an indication of the presence, or as a measure of the amount and optionally the location, of analyte in the sample. In these embodiments, the ligated product comprises a single stranded nucleic acid molecule (which is the product of the ligation of the two proximal nucleic acid domains of the first and second probes, and any intermediary cassette oligonucleotide, if used) terminating at each end in an analyte binding domain.

The next step of the method following the conjugation (e.g. ligation) step is to determine the presence of the conjugated (e.g. ligated) product in the reaction mixture in order to detect the target analyte in the sample. In other words, the reaction mixture is screened etc. (i.e., assayed, assessed, evaluated, tested, etc.) for the presence of any resultant conjugation (ligation) products in order to detect the presence of the target analyte in the sample being assayed.

The conjugated (ligated) product produced by the above-described methods may, in the broadest sense, be detected using any convenient protocol. The particular detection protocol may vary depending on the sensitivity desired and the application in which the method is being practiced. In certain embodiments, the nucleic acid ligation product may be directly detected without any amplification, while in other embodiments the detection protocol may include an amplification component, in which the copy number of the ligated product nucleic acid is increased, e.g., to enhance sensitivity of the particular assay. Where detection without amplification is practicable, the nucleic acid ligation product may be detected in a number of different ways. For example, one or more of the nucleic acid domains of the proximity probes may be directly labeled, e.g., fluorescently, or otherwise spectrophotometrically, or radioisotopically labeled or with any signal-giving label, such that the ligation product is directly labeled. In these embodiments, the directly labeled ligation product may be size separated from the remainder of the reaction mixture, including unligated directly labeled ligation oligonucleotides (i.e. nucleic acid domain oligonucleotides or cassette oligonucleotides), in order to detect the ligated nucleic acid. Alternatively, conformationally selective probes, e.g., molecular beacons (as described in greater detail below) may be employed to detect to the presence of the ligation product, where these probes are directed to a sequence that spans the ligated nucleic acids and therefore only exists in its entirety in the ligation product.

As indicated above, in certain embodiments of the subject methods, the detection step includes an amplification step, where the copy number of ligated nucleic acids is increased, e.g., in order to enhance sensitivity of the assay. The amplification may be linear or exponential, as desired, where representative amplification protocols of interest include, but are not limited to: polymerase chain reaction (PCR); isothermal amplification, etc.

Where the detection step includes an amplification step (more specifically a step of in vitro amplification of the conjugated product), the amplified product (or amplification product) may be detected, to detect the analyte.

The polymerase chain reaction (PCR) is well known in the art, being described in U.S. Pat. Nos. 4,683,202; 4,683,195; 4,800,159; 4,965,188 and 5,512,462, the disclosures of which are herein incorporated by reference. In representative PCR amplification reactions, the reaction mixture that includes the above ligated nucleic acids or ligation product (which may also be viewed as a template nucleic acid in an amplification reaction) is combined with one or more primers that are employed in the primer extension reaction, e.g., the PCR primers (such as forward and reverse primers employed in geometric (or exponential) amplification or a single primer employed in a linear amplification). The oligonucleotide primers with which the template nucleic acid hereinafter referred to as template DNA for convenience) is contacted will be of sufficient length to provide for hybridization to complementary template DNA under annealing conditions (described in greater detail below). The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired.

In addition to the above components, the reaction mixture produced in the subject methods typically includes a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Barnes et al, Proc. Natl. Acad. Sci USA (1994) 91:2216-2220); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcuss litoralis* DNA polymerase (Vent) as described in Perler et al., Proc. Natl. Acad. Sci. USA (1992) 89:5577-5581; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Where the reaction mixture includes both a Family A and Family B polymerase, the Family A polymerase may be present in the reaction mixture in an amount greater than the Family B polymerase, where the difference in activity will usually be at least 10-fold, and more usually at least about 100-fold. Usually the reaction mixture will include four different types of dNTPs corresponding to the four naturally occurring bases present, i.e. dATP, dTTP, dCTP and dGTP. In the subject methods, each dNTP will typically be present in an amount ranging from about 10 to 5000 µM, usually from about 20 to 1000 µM.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulphate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reaction mixture of this step of the subject methods, the various constituent components may be combined in any convenient order. For example, the buffer may be combined with primer, polymerase and then template DNA, or all of the various constituent components may be combined at the same time to produce the reaction mixture.

The amplified products of the amplification reaction may be detected using any convenient protocol, where the particular protocol employed may detect the amplification products non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4,6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR, SYTO, SYTOX PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the amplification product, as opposed to double stranded molecules in general, may be employed to detect the amplification. In these embodiments, the signal producing system may include a probe nucleic acid that specifically binds to a sequence found in the amplification product, where the probe nucleic acid may be labeled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labeling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labeled probe nucleic acids include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labeled probe nucleic acids are labeled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others' electronic structure. If the fluorescence-modifying group is a quenching group, this will result in the quenching group preventing the fluorescent group from even emitting light.

The energy transfer labeled probe nucleic acid, e.g., oligonucleotide, may be structured in a variety of different ways, so long as it includes a donor, acceptor and target nucleic acid binding domains. As such, the energy transfer labeled oligonucleotides employed in these embodiments of the method are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector. The acceptor domain includes the fluorescence energy acceptor. The acceptor may be positioned anywhere in the acceptor domain, but is typically present at the 3' terminus of the nucleic acid detector or probe.

In addition to the fluorophore and acceptor domains, the energy transfer labeled probe oligonucleotides also include a target nucleic acid binding domain, which binds to a target nucleic acid sequence found in the amplification product of interest (as described above), e.g., under stringent hybridization conditions (as defined above). This target binding domain typically ranges in length from about 10 to about 60 nucleotides, usually from about 15 to about 30 nt. Depending on the nature of the oligonucleotide and the assay itself, the target binding domain may hybridize to a region of the template nucleic acid or a region of the primer extension product. For example, where the assay is a 5' nuclease assay, e.g., in which a TaqMan® type oligonucleotide probe is employed, the target binding domain hybridizes under stringent conditions to a target binding site of the template nucleic acid, which is downstream or 3' of the primer binding site. In alternative embodiments, e.g., in molecular beacon type assays, the target binding domain hybridizes to a domain of a primer extension product. The overall length of the energy transfer labeled oligonucleotides employed in these embodiments, which includes all three domains mentioned above, typically ranges from about 10 to about 60 nucleotides, usually from about 15 to about 30 nucleotides.

In certain embodiments, the energy transfer labeled oligonucleotide is structured such that energy transfer occurs between the fluorophore and acceptor of the energy transfer labeled oligonucleotide probe upon fluorophore excitation when the energy transfer labeled oligonucleotide is not hybridized to target nucleic acid.

In certain embodiments, the oligonucleotide is a single stranded molecule that does not form intramolecular structures and in which energy transfer occurs because the spacing of the donor and acceptor provides for energy transfer in the single stranded linear format. In these embodiments, energy transfer also occurs between the fluorophore and acceptor of labeled oligonucleotide probe upon fluorophore excitation when the labeled oligonucleotide probe is hybridized to a target nucleic acid. Specific examples of such labeled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). In many of these embodiments, the target nucleic acid binding domain is one that hybridizes to, i.e., is complementary to, a sequence of the template nucleic acid, i.e., the target nucleic acid of the target nucleic acid binding domain is a sequence present in the template nucleic acid (i.e., the pseudotarget or surrogate nucleic acid).

In other embodiments, the probe oligonucleotides are structured such that energy transfer does not occur between the fluorophore and acceptor of the energy transfer labeled oligonucleotide probe upon fluorophore excitation when the energy transfer labeled oligonucleotide probe is hybridized to a target nucleic acid. Examples of these types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference). In many of these embodiments, the target binding sequence or domain comprises a hybridization domain complementary to a sequence of the primer extension product of the amplification reaction, and not to a sequence found in the pseudotarget nucleic acid.

The next step in the subject methods is signal detection from the labeled amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signaling moiety (i.e. fluorophore). The areas under the peaks can be determined which represents the intensity value for each signal, and if required, expressed as quotients of each other. The differential of signal intensities and/or ratios will allow changes in labeled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target analyte present in the sample, e.g., as correlated to the amount of amplification product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of target analyte(s). The methods are suitable for detection of a single target analyte as well as multiplex analyses, in which two or more different target analytes are assayed in the sample. In these latter multiplex situations, the number of different sets of probes that may be employed typically ranges from about 2 to about 20 or higher, e.g., as up to 100 or higher, 1000 or higher, etc.

The analysis of many analytes simultaneously and in a single reaction using several different proximity ligation probe sets (multiplexing) is made possible by the increased specificity and sensitivity obtained with the binding splint method. Each probe set can be designed to produce a unique ligation product that can be used to determine the presence or absence, quantity and/or location of the analytes being interrogated by the probe set. The ligation product may be detected directly or after amplification using any of the well established methods for analysis of nucleic acid molecules known from the literature including liquid chromatography, electrophoresis, mass spectrometry, microscopy, real-time PCR, fluorescent probes etc. Of particular interest is the combination of the binding splint method with a "DNA array" readout format. Several unique ligation products from a multiplexed proximity ligation assay may be hybridized to a standardized DNA array carrying a number of oligonucleotide sequences (tags) complementary to the ligation product sequences. Each ligation product hybridized to the array may be identified by its location on the DNA array and the detected intensity in a given hybridization spot will be indicative of the quantity of that specific ligation product and hence also of the analyte giving rise to that ligation product. Detection of the ligation products may be accomplished by spectrometry, fluorescence, radioisotopes etc. Fluorescent moieties may conveniently be introduced into the ligation products using fluorescently labelled primers or fluorescently labelled nucleotides in the amplification reaction (PCR). The DNA array may be a simple dot-blot array on a membrane containing a small number of spots or a high density array carrying hundreds of thousands of spots.

The method of the invention may be modified in order to reduce the background associated with non-specific nucleic acid hybridization events. Such modifications include adjustments to the method that will reduce any non-specific nucleic acid hybridization events. In some embodiments, a protein may be added to the mixture containing the sample and the proximity probes in order to reduce weak and non-specific DNA hybridization events. For example, $E.$ $coli$ single strand DNA binding protein has been used to increase the yield and specificity of primer extension reactions and PCR reactions. (U.S. Pat. Nos. 5,449,603 and 5,534,407.) The gene 32 protein (single strand DNA binding protein) of phage T4 apparently improves the ability to amplify larger DNA fragments (Schwartz, et al., Nucl. Acids Res. 18: 1079(1990)) and enhances DNA polymerase fidelity (Huang, DNA Cell. Biol. 15: 589-594 (1996)). When employed, such a protein will be used to achieve a concentration in the reaction mixture that ranges from about 0.01 ng/µL to about 1 µg/µL; such as from about 0.1 ng/µL to about 100 ng/µL; including from about 1 ng/µL to about 10 ng/µL.

In other embodiments, double stranded nucleic acid may be used as the nucleic acid domain of the first and second proximity probes in order to reduce weak and non-specific DNA hybridization events.

As explained above, the method of the invention is designed such that interaction between the nucleic acid domains of the first and second probes (conjugation) should occur only if all three probes are bound to the analyte. However, as is the case with all assays of this type, this cannot always be guaranteed and there may be some background interaction, or conjugation of the nucleic acid domains, if the three probes come into proximity randomly in solution (the possibility of this is reduced by requiring the nucleic acid domains of all three probes to hybridise to one another by means of the splint, in order for such interaction to occur; the chances of all three domains coming into proximity randomly are reduced, compared to two-probe assays, nonetheless this may still under some circumstances occur). To reduce or minimise the possibility of background due to unreacted (i.e. unbound) probes, blocking oligonucleotides may be used.

The blocking oligonucleotides bind (i.e. hybridise or anneal) to the free ends of the nucleic acid domains of the first and second proximity probes. Thus a blocking oligonucleotide may bind to the free 3' OH end of the nucleic acid domain of a 5' proximity probe and to the free 5' phosphate end of the nucleic acid domain of a 3' proximity probe. The binding of the blocking oligonucleotide may be out-competed in the presence of a high local concentration of the splint, such as occurs when all three probes are bound together on the analyte. In this way the blocking oligonucleotide may prevent the first and second domains from hybridising to the splint on the third proximity probe in the absence of analyte binding. Thus the free ends of the 5' and 3' probes may be prevented from interaction in the absence of binding to the analyte. When all three probes are bound to the analyte, the local concentration of the splint is sufficient to out-compete the blocking oligonucleotides; the first and second domains hybridise to the splint and the blocking oligonucleotides are replaced.

The blocking oligonucleotides thus allow a competition-based strategy to be used to reduce background and thus increase sensitivity of the assay.

The blocking oligonucleotides may range in length from about 4-100 nucleotides, e.g. 6-75 or 10-50. They may hybridise to a region at or near the free end of the nucleic acid domain of the first or second probe ("near" meaning within 1-20 or 1-10, e.g. 1-6 nucleotides of the free 3' or 5' end). The region of hybridisation may be 3-15 nucleotides long e.g. 3-12, 3-10, 3-8, 4-8, 3-6, 4-6.

The blocking oligonucleotides may conveniently be designed to have a hairpin structure (e.g. as shown schematically in FIG. 1) such that the blocking oligonucleotide may be ligated to the end of proximity probes which have failed to hybridise to the splint.

The blocking oligonucleotides are typically used in an excess over the respective probes, e.g. an excess of 2-1000 fold, e.g. 20-500, 50-300, 100-500, or 100-300 fold e.g., 20, 200 or 300 fold.

In the case of detecting an analyte with proximity-probes of low affinity and slow binding kinetics, a preincubation step with the proximity-probes at a sufficiently high concentration promotes binding of the proximity probes to the analyte. This preincubation step may be quickly diluted in a large volume of cold buffer (e.g., buffer that does not include the analyte or the proximity probes), and a portion of this dilution subsequently added to a ligation reaction mixture. This ligation reaction mixture may contain the cassette oligonucleotide (if used), ATP and ligase enzyme. The low temperature, e.g., ranging from about 0° C. to about 20° C., including from about 4° C. to about 10° C., minimizes the dissociation of existing proximity-probe-analyte complexes while the vast dilution results in a decrease of the concentration of the unbound proximity-probes, thereby lowering their reactivity and minimizing the background signal.

In such embodiments, the assay is performed by using a small incubation volume of from about 1 µl to about 20 µl, such as about 1 µl, or about 2 µl, or about 3 µl, or about 4 µl, or about 5 µl or about 6 µl, of sample and proximity probes and then adding the cassette in a larger incubation volume of from about 8 µl to about 1.5 ml or more, such as from about 20 µl to about 1.3 ml, such as from about 50 µl, to about 1 ml, such as from about 75 µl to about 800 µl, such as from about 100 µl to about 500 µl, such as from about 200 µl to about 300 µl. The effective concentration of the proximity probes in the final incubation volume is thus diluted, reducing the background while maintaining the signal since the binding between the probes and analyte does not have time to dissociate before the first and the second nucleic acid domains are ligated. This approach enables extremely high sensitivity as long as the ligation products can be concentrated from the larger volumes, such as over 100 µl or more, and then detecting the proximity dependent interaction. In such embodiments, the probe-probe interactions can be reduced by using single strand binding proteins.

Problems associated with complex samples may be addressed by diluting the complex sample prior to the analysis. This will greatly decrease the amount of proteins the probes may bind unspecifically to thereby lowering concentration of probes required. While the analyte will also be diluted, the high sensitivity of the proximity probing will provide good detection and quantification.

The binding splint method of the present invention may be employed homogeneously (i.e. in solution) as described above, or alternatively heterogeneously, using a solid phase, for example, in which bound analyte becomes immobilised on a solid phase, permitting the use of washing steps. The use of solid phase assays offers advantages, particularly for the detection of difficult samples: washing steps can assist in the removal of inhibiting components, and analytes can be enriched from an undesirably large sample volume. Higher concentrations and greater amounts of proximity probes can be used, as unbound analytes and probes can be removed by washing. The ability to remove unbound or unconjugated probes by washing also means that the solid phase assay tolerates lower purity proximity probes by comparison with the homogeneous assay.

Immobilisation of the analyte on a solid phase may be achieved in various ways. Accordingly, several embodiments of the solid phase binding splint assay are contemplated. In one such embodiment, one (or more) of the first, second or third proximity probes may be (or may be capable of being) immobilised on a solid phase (or solid support). The analyte can firstly be captured by the one (or more) immobilised (or immobilisable) probes and secondly be bound by subsequently added probe(s). In such a scheme, the previously-mentioned avidity effect may not be present during the binding step but is relevant for the washing steps. Preferably, the analyte is contacted with the solid phase-bound (i.e. immobilised, or immobilisable) probe(s) at the same time as the non-immobilised/non-immobilisable probe(s) are added to the reaction mixture, such that the avidity effect contributes also to the detection (binding) step.

The immobilised proximity probe may be immobilised, i.e. bound to the support, in any convenient way. Thus the manner or means of immobilisation and the solid support may be selected, according to choice, from any number of immobilisation means and solid supports as are widely known in the art and described in the literature. Thus, the probe may be directly bound to the support, for example via the analyte-binding domain (e.g. chemically crosslinked), it may be bound indirectly by means of a linker group, or by an intermediary binding group(s) (e.g. by means of a biotin-streptavidin interaction). Thus, a proximity probe may be provided with means for immobilisation (e.g. an affinity binding partner, e.g. biotin or a hapten, capable of binding to its binding partner, i.e. a cognate binding partner, e.g. streptavidin or an antibody) provided on the support. The probe may be immobilised before or after binding to the analyte. Further, such an "immobilisable" probe may be contacted with the sample together with the support.

The solid support may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10, and e.g. not more than 6 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the analyte binding steps.

In another embodiment, an immobilised (or immobilisable) analyte-specific probe comprising only a binding domain (i.e. an analyte capture probe) can be used in addition to the three non-immobilised proximity probes of the homogeneous binding splint assay. Thus in such an embodiment the analyte is first captured by the immobilised or immobilisable capture probe which serves only to immobilise the analyte on the solid phase, and subsequently the immobilised analyte is incubated with the three "binding splint" proximity probes. In such an embodiment, the capture probe may be any binding partner capable of binding the analyte, directly or indirectly (e.g. as discussed above in relation to the analyte-binding domain of the proximity probe). More particularly, such a capture probe binds specifically to the analyte. Since this embodiment of the method requires the simultaneous binding of four probes (binding domains) to the analyte or analyte complex, potentially four different epitopes can be interrogated, conferring high specificity on the assay.

In a further embodiment, the analyte itself may be immobilised (or immobilisable) on the solid phase e.g. by non-specific absorption. In a particular such embodiment, the analyte may be present within cells, being optionally fixed and/or permeabilised, which are (capable of being) attached to a solid support.

The above-described methods result in detection of splint-mediated proximity dependent interactions that are present in the reaction mixture, which in turn provides a measure of the amount of target analyte in the sample being assayed. The measure may be qualitative or quantitative Accordingly, the above described methods of detecting the presence of one or more target analytes in a complex sample finds use in a variety of different applications.

The subject methods may be used to screen a sample for the presence or absence of one or more target analytes in a sample. As indicated above, the invention provides methods of detecting the presence or quantifying the amount of one or more target analytes in a sample.

The subject methods can be employed to detect the presence of one or more target analytes in a variety of different types of samples, including complex samples having large amounts of non-target entities, where the subject methods provide for detection of the target analytes(s) with high sensitivity. As such, the subject methods are highly sensitive methods of detecting one or more target analytes in a simple or complex sample. The sample that is assayed in the subject methods is, in many embodiments, from a physiological source, as discussed in more detail above.

In addition to detecting a wide variety of analytes, the subject methods may also be used to screen for compounds that modulate the interaction between the analyte binding domain of the proximity probe with the binding region of the analyte i.e. the binding of the analyte-binding domain to the analyte. The term modulating includes both decreasing (e.g., inhibiting) and enhancing the interaction between the two molecules. The screening method may be an in vitro or in vivo format, where both formats are readily developed by those of skill in the art.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays find use in the a variety of methods, including methods of modulating the activity of the target analyte, and conditions related to the presence and/or activity thereof.

Also provided are kits that find use in practicing the subject methods, as described above. For example, in some embodiments, kits for practicing the subject methods include at least one set of proximity probes, which proximity probes each include an analyte binding domain and a nucleic acid domain as described above. As indicated above, the certain protocols will employ two or more different sets of such probes for simultaneous detection of two or more target analytes in a sample, e.g., in multiplex and/or high throughput formats. As such, in certain embodiments the kits will include two or more distinct sets of proximity probes. Furthermore, additional reagents that are required or desired in the protocol to be practiced with the kit components may be present, which additional reagents include, but are not limited to: a ligase, cassette oligonucleotide, blocking oligonucleotides, solid support for immobilisation of probe, binding domain or analyte, means for immobilisation of probe, binding domain or analyte, detection means e.g. fluorescently labelled nucleotides or oligonucleotides, pairs of supplementary nucleic acids, single strand binding proteins, and PCR amplification reagents (e.g., nucleotides, buffers, cations, etc.), and the like. In certain embodiments, the kits may include elements employed in reducing the effective volume of an incubation mixture, as reviewed above, e.g., a volume excluder. The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Accordingly, in a further aspect the present invention provides a kit for use in method for detecting an analyte in a sample, said kit comprising:

(a) at least one set of at least first, second and third proximity probes, which probes each comprise an analyte-binding domain and a nucleic acid domain and can simultaneously bind to the analyte, the nucleic acid domain of said third proximity probe being a splint which is capable of hybridising at least to the nucleic acid domains of said first and second proximity probes, wherein when all of the at least three proximity probes bind to said analyte, the nucleic acid domains of said first and second proximity probes are conjugatable by means of an interaction mediated by said hybridised splint;

(b) optionally, means for conjugating the nucleic acids of said first and second proximity probes; and (c) optionally, means for detecting said conjugation.

As indicated above, the means for conjugation may be a ligase enzyme, and such means may optionally further comprise the reagent necessary for the ligase reaction (e.g. nucleotides etc). The means for detecting the conjugation, may be any of the means discussed above in the context of the assay methods e.g. a label provided on the nucleic acid domains of the first and second probe or it may be amplification means and means for detecting amplification products thereof e.g. reagents for a PCR reaction (e.g. amplification primers, and optionally polymerase and/or nucleotides, etc.) and for detecting PCR amplicons etc (e.g. Taqman® probes etc.).

The kit may further optionally comprise a cassette oligonucleotide and/or blocking oligonucleotides for the first and second probes.

The kit may further optionally comprise an immobilised capture probe for the analyte, or a capture probe provided with means for immobilisation. Alternatively, the kit may comprise a solid phase for capture of, or binding to, the analyte, or one or more said first, second or third proximity probes may be immobilised or provided with means for immobilisation.

The invention will be further described with reference to the following non-limiting Examples:

Example 1

The method of the invention was used to detect different proteins.

Vascular endothelial growth factor (VEGF) is a homodimeric, 42 kDa cytokine which at low concentrations stimulates growth of blood vessels. Detection of VEGF was carried out using an affinity-purified polyclonal antiserum that was split in two or three aliquots, respectively, for the two-probe, free splint assay and the binding splint assay of the present invention, and conjugated to the appropriate oligonucleotides (Table 1).

TABLE 1

| Name | Sequence | Modification | Company | SEQ ID NO |
|---|---|---|---|---|
| L8560 Proximity probe arm 3' free | CGCATCGCCCTTGGACTACGACTGACGA ACCGCTTTGCCTGACTGATCGCTAAATCGTG | 5' Aldehyde | TriLink | 1 |
| L8561 Proximity probe arm 5' free | TCGTGTCTAAAGTCCGTTACCTTGATTC CCCTAACCCTCTTGAAAAATTCGGCATCGGTGA | 5' Phosphate 3' Aldehyde | TriLink | 2 |
| L8562 Proximity probe arm hybridization | TAGCTAAGGCTTAGTTAGACACGAGCA TTATGGAGTGCAGGATCACGATTTAG | 3' Aldehyde | TriLink | 3 |
| L8388 Primer Fwd | CATCGCCCTTGGACTACGA | | Biomers | 4 |
| L8389 Primer Rev | GGGAATCAAGGTAACGGACTTTAG | | Biomers | 5 |
| X00555 linker oligo | ATCCTGCACTCCATAATGC | 5' Phosphate | Eurogentec | 6 |
| L8407 Splint | TACTTAGACACGACACGATTTAGTTT | | Biomers | 7 |

The 33 kDa protein prostate-specific antigen (PSA) is an important biomarker for the screening of prostate cancer in men. PSA forms complexes with other proteins such as alpha 1-antichymotrypsin (ACT) or alpha 1-protease inhibitor (API). Measurement of the ratio of these complexes to free PSA has been shown to improve the distinction of prostate cancer from benign prostate diseases, compared to assays measuring total PSA levels. We took advantage of the ability of the present invention to interrogate several determinants by choosing a suitable set of antibodies to evaluate interaction between PSA and one of its carrier proteins. Two monoclonal antibodies against PSA along with one directed at ACT were converted to proximity probes by attachment of suitable oligonucleotides. Total PSA was detected using proximity probes with oligonucleotide strands conjugated directly to the three monoclonal antibodies using hydrazone chemistry.

Finally, we developed proximity probes using a set of three monoclonal antibodies that were selected to bind three independent determinants on human cardiac troponin I. This 29 kDa protein is currently the gold standard for the identification of patients at high-risk of having suffered myocardial infarction, as elevated levels of the protein in peripheral blood suggests damage to myocardial tissue. Assays with increased detection sensitivity could allow the identification of very small lesions of short duration, thereby potentially allowing the infarction to be reversed through therapeutic intervention before extensive tissue damage has developed.

Methods

VEGF and affinity-purified polyclonal antibodies specific for VEGF were from R&D Systems, while reagents for the PSA-ACT assay were provided by Ulf Håkan Stenma, Helsinki and the troponin assays were provided by Kim Pettersson (Turku). The monoclonal PSA antibodies for detecting free PSA were purchased from Biodesign. Oligonucleotides were attached at their 3' or 5' ends to two aliquots of a polyclonal antibody recognizing total PSA, and the third oligonucleotides, capable of hybridizing to the other two, was conjugated to an antibody recognizing free PSA. Covalently conjugated oligonucleotides were purchased from Solulink, USA (conjugation) and Trilink, USA (oligonucleotides) in collaboration with Olink (Sweden). Sequences of the oligonucleotide are shown in Table 1.

Oligonucleotides were coupled to streptavidin (SA) using two different protocols as described in Gullberg et al (2004) Proc Natl Acad Sci USA 101:8420-8424, and a novel hydrazine based conjugation strategy. Maleimide-derivatized SA (0.5 nmol) (Sigma) was coupled to 2 nmol of DTT-reduced oligonucleotides with 3' or 5' sulphydryls in 50 µl of phosphate-buffered saline with 5 mM EDTA. Reduction was performed in a 50 µl volume of 50 mM freshly prepared DTT with 2% triethylamine for 10 min at RT. Excess DTT was removed by centrifugation through a spin out 6000 column (Chemicon) at 1,500 g for 1 min. The eluate was directly combined with the maleimide-derivatized SA for 2 h at RT. Crude conjugates were purified from free DNA by protein precipitation with 1 volume of saturated ammonium sulphate at 65° C. for 2 h, then centrifuged at RT for 30 min at 13,000 g. The supernatant was removed, the precipitate redissolved in phosphate buffered saline with 5 nM EDTA, and the protein precipitation process was repeated once more. The conjugates were purified by DNA precipitation with 0.1 volume of 3 M NaAc, pH 4.6, 10 mM $Mg(Ac)_2$, and 2 volumes of ice-cold 95% ethanol. After 2 h at RT, the sample was centrifuged at 13,000 g for 30 min at 4° C. The final product was dissolved in 50 µl of 10 mM Tris-HCl pH 7.4, with 0.02% sodium azide and stored at 4° C. The oligonucleotide concentration was determined by absorbance measurements at 260 nm with a NanoDrop spectrophotometer and the conjugates were characterized on a Genegel Excel 12.5 Kit (Amersham) using an automated silver staining system (Amersham).

Alternatively, oligonucleotides were conjugated to SA using hydrazine aldehyde-based chemistry. Hydrazine-activated SA (Pierce) was added to aldehyde-activated oligonucleotides at a 1:1 ratio and left to react for at least 15 hours. Aldehyde-activated oligonucleotides were obtained from Trilink or by activating amine-modified oligonucleotides with an aldehyde-containing linker. (SanH, Pierce). The reacted conjugates were loaded on Genegel precast gels and run for 120 min. One lane of the gel was cut off and silver stained to be used as guidance for cutting out the conjugates from the rest of the gel. The conjugates were eluted from the gel in 1× PBS overnight followed by ethanol precipitation.

Biotinylated antibodies were bound to purified SA-oligonucleotide conjugates at a 1:1 ratio at 50 nM for 1 h at RT and they were stored at 4° C. for up to one month. Before use the conjugates were diluted from this stock as needed in PLA buffer (PBS with 1% BSA, 16 µg/ml sheared polyA bulk nucleic acid (Sigma), and 1 mM free biotin, added to quench any further biotin-SA interaction).

Unless otherwise indicated all two-probe, free splint assays were performed using 10 µl of final incubation volume. Proximity probes with free 3' and 5' ends were added at a final concentration of 50 pM and the protein sample was added in a volume of 1 to 8 µl, both diluted in PLA buffer. For the binding splint assays, the 3' and 5' ends, respectively, of oligonucleotides on two proximity probes were designed to hybridize to a third proximity probe leaving a stretch of 20 bp between them to form 2 independent ligation sites. These proximity probes were used at a concentration of 500 pM and a concentration of 100 nM blocking oligonucleotides 3' and 5 and combined with sample volumes between 1 and 8 µl in PLA buffer at a final volume of 10 µl for the incubation mix. The proximity probes and protein were incubated for 2 h for the VEGF and PSA-ACT assays and for 3 h for the troponin assays. Troponin assays of biological samples contained 5% heparin and citrate plasma added to the dilution buffer. After the incubation the combined mix for ligation and real-time PCR was added for a total volume of 50 µl, containing 50 mM KCl, 10 mM Tris-HCl pH 8.3, 1.5 mM $MgCl_2$, 0.4 units T4 DNA ligase (Fermentas, Germany), 400 nM splint oligonucleotide for free splint assays or 40 nM cassette oligonucleotide for binding splint assays, 80 µM ATP, 0.2 mM of each dNTP, 0.5 µM primers (Table 1), 200 nM MGB TaqMan probe (ABI, Foster City, USA) and 0.3 units Platinum Taq polymerase (Invitrogen). After 5 min ligation at room temperature the reactions were transferred to a real time PCR instrument for temperature cycling: 2 min at 95° C. and then 15 s at 95° C. and 60 s at 60° C., repeated 45 times (ABI 7000, MX3000 Stratagene).

Results

Figure 2:
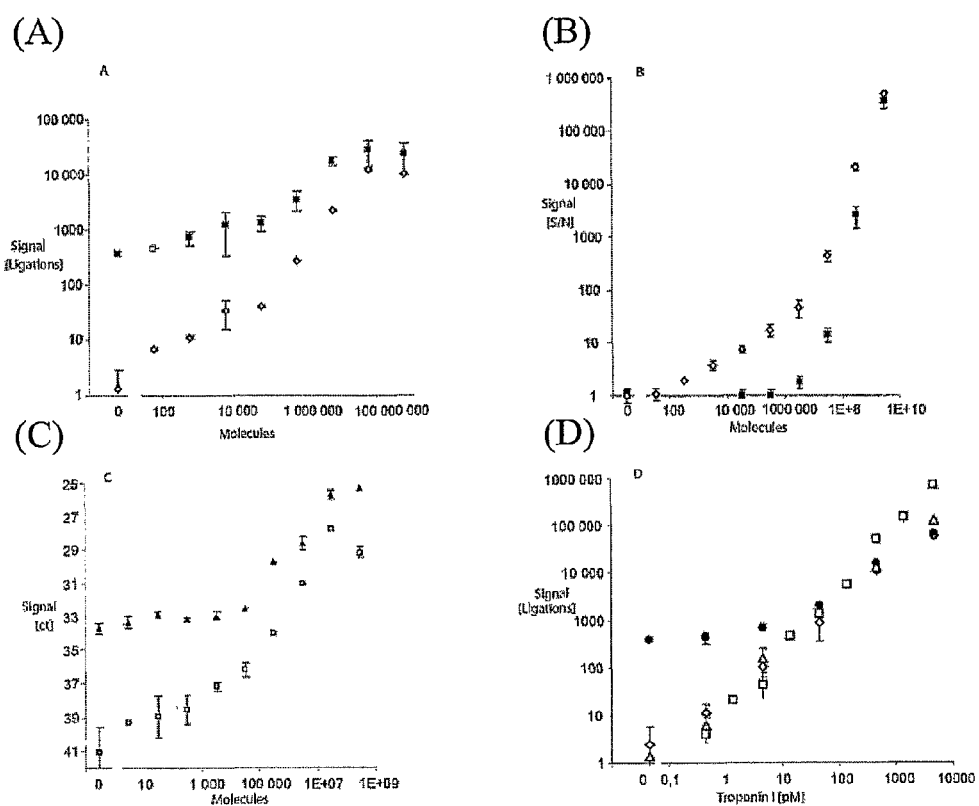
FIG. 2A: Detection of VEGF in homogenous format comparing the two-probe, free splint assay (squares) and the binding splint assay of the present invention (diamonds) using a split polyclonal antibody batch. The binding splint assay improves the sensitivity approx 100-fold in this assay.
FIG. 2B: Detection of recombinant uncomplexed prostate-specific antigen (PSA) using two monoclonal antibodies against total PSA and one monoclonal antibody against free PSA for the binding splint assay (diamonds) and two monoclonal antibodies against total PSA for the two-probe, free splint assay (squares). The LOD (limit of detection) is 10,000-fold lower for the binding splint assay, detecting 300 molecules (two standard deviations) over background compared to 3,000,000 in the two-probe, free splint assay.
FIG. 2C: Detection of the PSA-ACT complex using two monoclonal antibodies against total PSA and one against PSA-ACT for the binding splint assay (squares) and one monoclonal antibody against total PSA and one against PSA-ACT for the free splint assay (triangles).
FIG. 2D: Detection of the biomarker Troponin I in buffer using the two-probe, free splint assay (circles) and using the binding splint assay (squares) having additionally been spiked in citrate (triangles) and heparin plasma (diamonds).

The free splint assay was previously shown to detect around 5000-times less VEGF than a commercially available sandwich ELISA test. However, the method of the invention exhibited a further one hundred-fold increase in sensitivity, with as little as 60 molecules of VEGF resulting in a signal that was significantly greater than background (FIG. 2A). In both assays one µl samples were combined with five µl proximity probe mixes. We observed a characteristic biphasic response to increasing amounts of target protein in the binding splint assay, with a lower than expected response to increasing target concentrations in the low concentration range. The biphasic response could possibly reflect incomplete kinetic reactions due to short incubation time, in this case 2 hr at 37° C.

As seen in FIG. 2C, it was possible to detect as little as 100 PSA-ACT protein complexes. We detected PSA-ACT with a molecular mass of 95 kDa in the presence of free PSA over a range from 100% down to 1% complexed protein vs. free protein, and the measurements had a coefficient of variance (CV) of 5% (0.06 pM) and 13% for (3.5 pM).

The standard curve in FIG. 2B shows the detection of only 300 molecules of recombinant uncomplexed PSA over background. This is 40,000-fold more sensitive than the corresponding two-probe, free splint assay or 2000-fold more sensitive than reported Immuno PCR assays and $2 \times 10^5$ times more sensitive than current Elisa techniques (Lind and Kubista (2005) J Immunol Methods 304:107).

The binding splint assay detected troponin I at as low concentrations as 0.3 pM in buffer, and importantly, the same sensitivity was observed in heparinized or citrate-heparin treated plasma (FIG. 2D). This is approximately 5-fold more sensitive than current clinical tests (Christenson et al (1998) Clin Chem 44:52-60; Zethelius et al (2006) Circulation 113; 1071-1078; Venge et al (2001) Clin Chem 47:959-961).

What is claimed is:

1. A method for detecting an analyte in a sample, comprising:
   (a) contacting said sample with at least one set of at least first, second and third proximity probes, which probes each comprise an analyte-binding domain and a nucleic acid domain and can simultaneously bind to the analyte, the nucleic acid domain of said third proximity probe being a splint which is capable of hybridizing at least to the nucleic acid domains of said first and second proximity probes, wherein when all of the at least three proximity probes bind to said analyte, the nucleic acid domains of said first and second proximity probes are directly or indirectly conjugatable by means of a ligation reaction templated by said hybridized splint of said third proximity probe;
   (b) conjugating the nucleic acids of said first and second proximity probes; and
   (c) detecting said conjugation thereby detecting said analyte.

2. The method as claimed in claim 1, wherein said detecting is quantitative.

3. The method as claimed in claim 1, wherein said detecting is qualitative.

4. The method as claimed in claim 1, wherein the analyte is a wholly or partially proteinaceous molecule.

5. The method as claimed in claim 1, wherein the analyte is a complex of two or more molecular subunits.

6. The method as claimed in claim 5, wherein said complex comprises nucleic acid and proteinaceous molecules.

7. The method as claimed in claim 1, wherein the analyte binding domain of at least one of said at least first, second and third proximity probes is an antibody, or a binding fragment or derivative thereof.

8. The method as claimed in claim 1, wherein at least one of said at least first, second and third proximity probes binds to said analyte indirectly by virtue of the respective analyte-binding domain having affinity for an intermediary molecule which binds directly to the target analyte.

9. The method as claimed in claim 1, wherein the nucleic acid domains of said first and second proximity probes hybridize, immediately adjacent to each other to the nucleic acid domain of said third proximity probe.

10. The method as claimed in claim 1, wherein the nucleic acid domains of said first and second proximity probes hybridize, not immediately adjacent to each other, to the nucleic acid domain of said third proximity probe, such that when hybridized to the nucleic acid domain of said third proximity probe the nucleic acid domains of said first and second proximity probes are separated by a gap.

11. The method as claimed in claim 10, wherein a cassette oligonucleotide hybridizes to the nucleic acid domain of said third proximity probe in the gap between the respective ends of the nucleic acid domains of said first and second proximity probes hybridized to the nucleic acid domain of said third proximity probe.

12. The method as claimed in claim 11, wherein conjugation of the nucleic acid domains of said first and second proximity probes occurs indirectly through the cassette oligonucleotide.

13. The method as claimed in claim 10, wherein said gap between the nucleic acid domains of said first and second proximity probes is filled by enzymatic extension of the end of one of said first and second proximity probe nucleic acid domains.

14. The method as claimed in claim 1, wherein two or more sets of the at least first, second and third proximity probes are used, for detecting two or more analytes.

15. The method according to claim 1, wherein single strand binding protein is present in said contacting step.

16. The method according to claim 1, wherein blocking oligonucleotides capable of binding to the free ends of the nucleic acid domains of said first and second proximity probes are used in said contacting step.

17. The method according to claim 16, wherein said blocking oligonucleotides are pre-incubated with at least said first and second proximity probes.

18. The method according to claim 1, wherein at least one of said at least first, second and third proximity probes is immobilized, or is capable of being immobilized, on a solid phase.

19. The method according to claim 1, further comprising, prior to contacting said sample with the at least one set of at least first, second and third proximity probes, immobilizing the analyte to a solid phase by means of an immobilized, or immobilizable, capture probe comprising an analyte-binding domain.

20. The method according to claim 1, wherein the analyte is directly immobilized, or immobilizable, to a solid phase.

21. The method according to claim 1, wherein the analyte and the at least one set of at least first, second and third proximity probes are free in solution.

22. The method of claim 1 wherein the step of detecting the conjugation includes detecting the conjugation product.

23. The method of claim 22, wherein detecting the conjugation product comprises amplifying the conjugation product and detecting the amplified product.

24. A kit for detecting an analyte in a sample, comprising at least one set of at least first, second and third proximity probes as defined in claim 1.

25. The kit as claimed in claim 24, further comprising:
   (a) means for conjugating the nucleic acid domains of said first and second proximity probes; and/or
   (b) means for detecting said conjugation.

26. The kit as claimed in claim 25 wherein said means for conjugating the nucleic acid domains of said first and second proximity probes comprises a nucleic acid ligase.

27. The kit as claimed in claim 25, wherein said means for detecting said conjugation is a label or means for amplification and/or the detection thereof.

28. The kit of claim 24 further comprising one or more of:
   (a) cassette oligonucleotide;
   (b) blocking oligonucleotides for the nucleic acid domains of said first and second proximity probes;
   (c) single strand binding protein;
   (d) immobilized or immobilizable capture probe comprising an analyte-binding domain; and
   (e) solid phase for immobilization of said analyte, capture probe or at least one of said at least first, second and third proximity probes.

* * * * *